United States Patent [19]

Liu et al.

[11] Patent Number: 5,354,681

[45] Date of Patent: Oct. 11, 1994

[54] ENZYME COMPLEX HYDROLYZING BACTERIAL CELL WALLS DERIVED FROM NOCARDIOPSIS DASSONVILLEI

[75] Inventors: Chi-Li Liu; Janet M. Overholt, both of Danbury, Conn.

[73] Assignee: 501 Novo Industri A/S, Bagsvaerd, Denmark

[21] Appl. No.: 196,619

[22] Filed: May 17, 1988

[51] Int. Cl.$^5$ .................. C12N 9/24; C12N 9/26; C12N 1/06

[52] U.S. Cl. .................. 435/200; 435/201; 435/252.1; 435/259; 435/822; 252/174.12

[58] Field of Search .......... 435/200, 201, 252.1, 435/259, 822; 252/174.12

[56] References Cited

U.S. PATENT DOCUMENTS

| | | | |
|---|---|---|---|
| 3,649,454 | 3/1972 | Isono et al. | 435/259 |
| 3,658,650 | 4/1972 | Okazaki | 435/259 |
| 3,682,778 | 5/1972 | Kawai et al. | 435/206 |
| 3,829,362 | 8/1974 | Horwath et al. | 435/94 |
| 4,828,998 | 5/1989 | Wöhner et al. | 435/206 |

OTHER PUBLICATIONS

American Type Culture Collection, Catalog of Bacteria, Phages and rDNA Vectors, Gherna (Ed.), 16th Edition, 1985, p. 123.
Chem. Abst. vol. 76, No. 25, Jun. 19, 1972, p. 325, Abst. 152061c.
Chem. Abst. vol. 103, No. 14, Oct. 7, 1985, Suzuki, Keitarou et al. "Serratia–lytic enzyme produced by . . . 177:, " p. 404.
Dialog Inf. Ser. File 5, Biosis, Biosis No. 84018801, Acc. No. 0017541741 "Actinomycetes of some hot . . . lytic activity".
Tibtech, vol. 5, Oct. 1987, pp. 273–277. Andrews et al. "Enzymatic Lysis and disruption of microbial cells".
Chem. Abst. vol. 112, No. 4, Jan. 1990, p. 114. Abst. 22800u.
Chem. Abst. vol. 99, No. 13, Sep. 26, 1983, Abst. 103739w.

*Primary Examiner*—Douglas W. Robinson
*Assistant Examiner*—L. Blaine Lankford
*Attorney, Agent, or Firm*—Steve T. Zelson; Elias J. Lambiris

[57] ABSTRACT

A bacteriolytic enzyme complex obtained from a bacterial culture of *Nocardiopsis dassonvillei* strains, e.g., isolates G102-3 (NRRL 18349), G119-6 (NRRL 18350), and D38-3 (NRRL 18364).

The enzyme complex may be produced by cultivating the microorganism in an aqueous medium containing maltodextrin and soybean meal, after which the lytic enzyme complex may be recovered from the fermentation broth.

This bacteriolytic enzyme complex is useful as a detergent additive.

11 Claims, 1 Drawing Sheet

THE pH-ACTIVITY PROFILE OF CRUDE LYTIC ENZYME FROM N. DASSONVILLEI STRAIN G102-3

THE pH-ACTIVITY PROFILE OF CRUDE LYTIC ENZYME FROM N. DASSONVILLEI STRAIN D38-3

ENZYME COMPLEX HYDROLYZING BACTERIAL CELL WALLS DERIVED FROM NOCARDIOPSIS DASSONVILLEI

The present invention relates to novel enzyme complexes capable of hydrolyzing bacterial cell walls both in buffer systems and in the presence of detergent components, to the process for preparing said enzymes, and to the use of these enzymes for reducing bacterial counts in laundry.

BACKGROUND OF INVENTION

The distinct malodorous scent of human adults, popularly called "body odor" has been found to be generated when microorganisms interact with apocrine sweat (J. J. Leyden et. al. J. Invest. Dermatol. 1981. 77:413–416). In a number of publications it has been suggested that the common skin microflora is a mixture of micrococcaceae, aerobic diphtheroids and propionic acid bacteria (J. J. Leyden et. al. 1981 & J. N. Labows et. al. J. Soc. Cosmet, Chem. 1982. 34: 193–202). The diphtheroids are responsible for the selective generation of the distinctly pungent odors, while the micrococci are responsible for the generation of sweaty, acid odors. The body odor problems in clothes has been of increasing concern because garments made from some synthetics hold odors and because an ever increasing popularity of physical exercise generates many garments permeated with sweat.

The detergent industry has long been using fragrances to make clothes smell fresh and to mask the unpleasant odor of the clothes. Also, "deoperfumes" have been introduced (e.g., into Surf TM) to react with odors and prevent them from evaporating and reaching the nose. However, the sources of odor production, microorganisms in the clothes, are not removed.

In addition to the above mentioned odor generating microorganisms, detergent manufacturers are also concerned about microorganisms found in laundry that might be pathogenic, such as *Pseudomonas aeruginosa* and *Staphylococcus aureus*.

Destroying the microorganism source(s) of body odor is believed to be a superior approach toward reducing generation of body odor in garments. This result might be achieved enzymatically during laundering.

Some enzymes including peptidases, (such as alanine amidase); glycosidases, (such as muramidase, or lysozyme); and autolysins (from a number of bacilli and bacteria species) are known to be capable of depolymerizing peptidoglycan of the microorganism cell wall. Their use during laundering might well cause lysis of the microorganisms which are on the clothes thereby rendering the microorganisms unviable, in effect disinfecting the laundry.

Some heretofore known bacteriolytic enzymes such as Mutanolysin from *Streptomyces globisporus* 1829 (ATCC 21553) and N-acetylmuramidase from *Streptomyces rutgersensis* (ATCC 3350) are capable of lysing some of the microorganisms involved with body odor but only in the absence of detergent components.

It is well documented that both Mutanolysin and N-acetylmuramidase from *Streptomyces rutgersensis* have pH optimum between 6–7. In consequence that the aforementioned enzymes showed low to no lytic activity in the presence of detergent formulations is not surprising.

Bacteriolytic enzymes with high lytic activity at alkaline pH levels (8–10) in the presence of detergent components have not been known heretofore.

SUMMARY OF INVENTION

It has now been discovered that certain *Nocardiopsis dassonvillei* strains elaborate extracellular enzyme complexes capable of hydrolyzing the cell walls of microorganisms present in household laundry, including for example micrococci, *Pseudomonas aeruginosa* and *Staphylococcus aureus*. These enzyme complexes are active under laundering conditions. Their use during a wash or rinse results in reduced contamination of clothes with common skin microflora, whereby the odor of the dirty clothes can be removed.

A more complete kill of target microorganisms is achieved by incorporating both a bacteriolytic (hereinafter termed lytic) enzyme complex of this invention and an alkaline Bacillus protease into the wash water solutions containing a detergent formulation.

DISCUSSION OF THE INVENTION

Use of the enzyme complexes of this invention on laundry has already been mentioned and they will be discussed further principally with reference to usage in laundering practices, such emphasis upon a preferred mode use being a convenient way to provide fulsome explanation of the invention. However, it should be understood that the bacteriolytic enzyme complexes of this invention may be used elsewhere for their lytic action, for example, in the meat packing industry to wash chicken, turkey, beef, etc. carcasses.

For any enzyme or enzyme complex to be useful in laundry practices, e.g., as a detergent additive, the enzyme complex must be active at alkaline pH levels and must not be inhibited by material components in the detergent formulation notably by the surfactant, the builder salts, and any chelating agents present (such as EDTA). Many heretofore known bacteriolytic enzymes, e.g., Mutanolysin (from *Streptomyces globisporus*) and N-acetylmuramidase (from *Streptomyces rutgersensis*) are relatively inactive in the presence of detergent components and/or at alkaline pH levels. The lytic enzyme complex of this invention is highly active at alkaline pH levels in the presence of detergent components.

The bacteriolytic enzyme complexes of this invention are elaborated extracellularly by *Nocardiopsis dassonvillei* strains productive of the lytic enzyme complex. Several lytic enzyme complex producing strains have been isolated i.e., *Nocardiopsis dassonvillei* strain G102-3 (NRRL 18349), strain G119-6 (NRRL 18350), and strain D38-3 (NRRL 18364) all of which secrete the enzyme complexes of the invention. On the other hand the *Nocardiopsis dassonvillei* type strain ATCC 23218 and the *Nocardiopsis mutabilis* type strain ATCC 31520 do not elaborate lytic enzyme complexs.

As may be expected in the instance of an enzyme complex, each of the different strains isolated as of the date hereof produce an individually differing lytic enzyme complex, the difference from one enzyme complex to another enzyme complex being in some proportion to a differing content of the individual enzyme activities present in the lytic enzyme complexes. The enzyme complex from the different strains were found to be more or less effective against individual (i.e., pure culture) test microorganisms. However, each of the lytic enzyme complexes were found to be effective to a significant degree against all of the test microorganisms.

According to a further aspect of this invention there is provided a method for producing the lytic enzyme complexes, a process which is characterized by cultivating a lytic enzyme producing strain of *Nocardiopsis dassonvillei* under aerobic conditions in a nutrient medium containing assimilable sources of carbon, nitrogen, and phosphorus, followed by recovery of the lytic enzyme complex from the fermentation broth. Known to the art aerobic growth conditions and nutrients for *Nocardiopsis dassonvillei* may be employed. Submerged fermentation is preferred.

A particularly advantageous feature of the present invention is that the lytic enzyme complex is compatible with and is most useful in combination with alkaline Bacillus proteases and in particularly with the commercially available alkaline Bacillus proteases commercially offered to and used by the soapers, e.g., Alcalase TM, Esperase TM, Savinase TM, Maxitase TM. Together protease and the lytic enzyme complex generate a combined, and perhaps synergistic bacteriolytic effect. Laundering tests on some target microorganisms using combinations of an alkaline Bacillus protease and a lytic enzyme complex has resulted more than a 90% kill level. A detergent additive which comprises a protease/lytic enzyme complex mixture is a preferred product mode of the invention.

Thus, a washing procedure forms part of this invention such procedure being characterized by carrying out an otherwise known in the art low temperature washing process, i.e., below about 40° C. for the wash water in the presence of 1000 to 20,000 units preferably 2000 to 10,000 units per liter of the lytic enzyme complex, preferably in the presence of 0.02 to 0.15 Anson units per liter of an alkaline Bacillus protease.

DETAILED DESCRIPTION OF THE INVENTION

Figure 1:
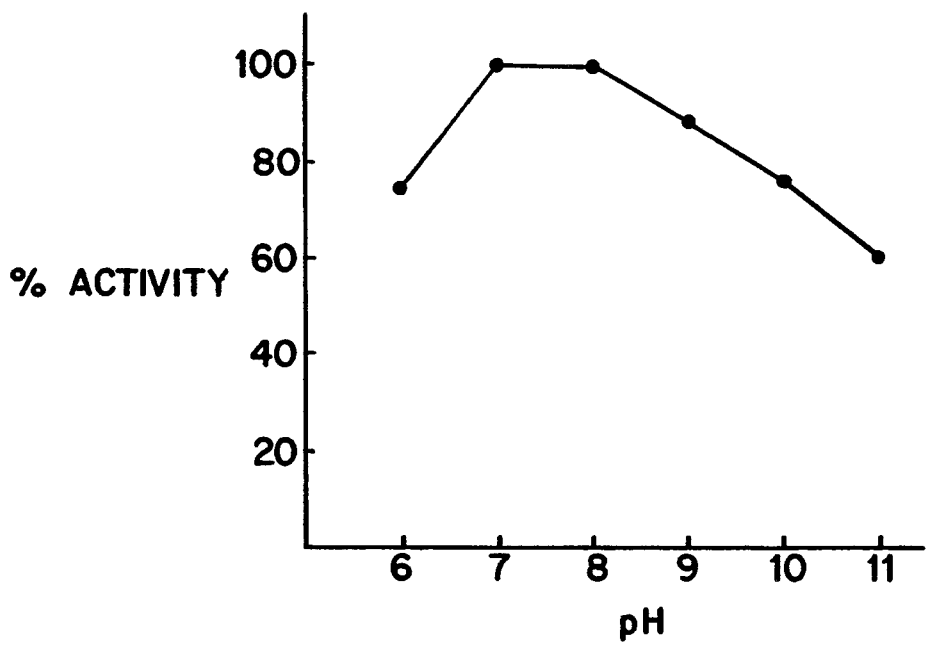

For further understanding of this invention, reference is made to the attached drawings wherein:

FIG. 1 graphically presents the lytic activity of crude enzyme broth from strain G102-3 toward *Staphylococcus aureus* cells as a function of pH.

Figure 2:
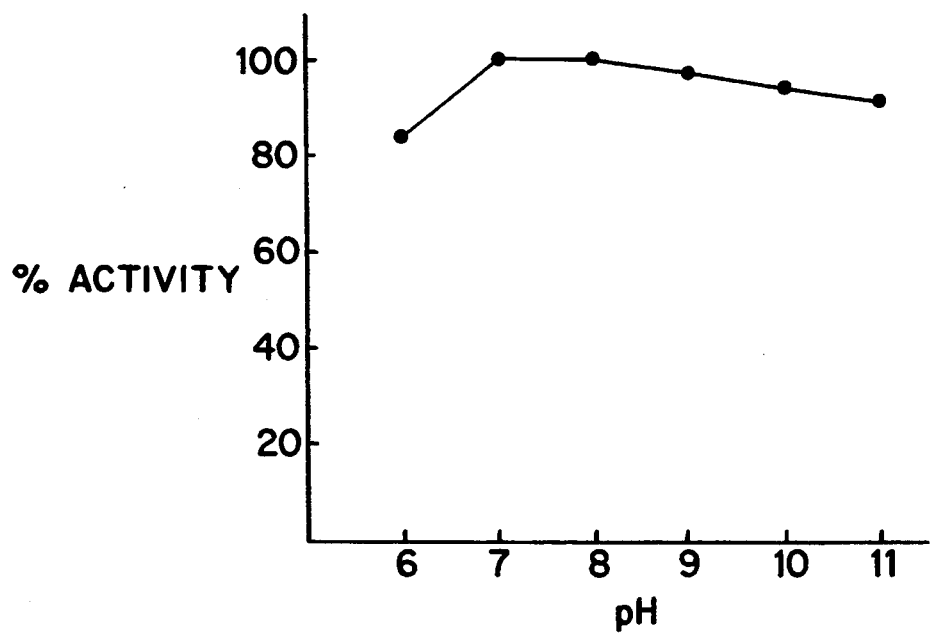

FIG. 2 graphically presents the lytic activity of Crude enzyme broth from strain D38-3 towards *Pseudomonas aeruginosa* cells as a function of pH.

The Microorganisms

The microorganisms of this invention are aerobic, actinomycete isolates of *Nocardiopsis dassonvillei*.

Three strains have been deposited at the Agricultural Research Culture Collection (NRRL), Peoria, Ill., U.S.A., under the terms of the Budapest Treaty, as follows:

| Depositor's reference | G102-3 | G119-6 | D38-3 |
|---|---|---|---|
| Deposit No. | NRRL 18349 | NRRL 18350 | NRRL 18364 |
| Deposit Date | 24 March, '88 | 24 March, '88 | 20 April, '88 |
| Taxonomic designation | Nocardiopsis dassonvillei | Nocardiopsis dassonvillei | Nocardiopsis dassonvillei |

Lytic enzyme producing mutants and variants of these strains thereby also within the scope of the invention, as is production of the lytic enzyme complex native to those strains from transformed host cells of other microorganism species (transformed by the recombinant DNA techniques known in the art). Temperature for growth of the above described strains is 25° C. to 35° C. with poor growth occurring at and above 35° C. Optimal pH for growth of strain G102-3 is 7 and is 8.5–9 for strains G119-6 and D38-3. No growth occurs at or below pH 7.0 for strains G119-6 and D38-3.

On nutrient agar slants, mature colonies of strain G119-6 exhibit mealy aerial mycelia with a faint creamy-yellow tint; as for strain D38-3, the mature colonies show a pinkish-beige cast. On Bennett's agar slants, mature colonies of strain G102-3 have rough, white to cream aerial mycelia.

Assay for Cell Wall Hydrolytic Activity

The cell wall hydrolytic activity in strain G102-3 and strain G119-6 and strain D38-3 cultures was determined by the turbidity reduction method (K. Hayashi et. al. Agric. Biol. Chem. 1981. 45(10):2289–2300). Viable or lyophilized target organisms, *Micrococcus kristinae* (ATCC 27570), *Micrococcus sedentarius* (ATCC 14392), *Pseudomonas aeruginosa* (ATCC 9027) and *Staphylococcus aureus* (ATCC 6538), are first suspended in 62.5 mM phosphate buffer, pH 7.0 to an OD at 660 nm of 0.8. To 2 ml of such a cell suspension, 0.5 ml of an appropriately diluted enzyme broth is added and the reaction mixture is incubated at 15° C. or 40° C. for 10 minutes. At the end of incubation time, the decrease in turbidity of cell suspension at 660 nm ($\Delta$ OD 660 nm) is measured by use of a spectrophotometer. One unit is defined as an amount of lytic enzyme which causes a decrease of 0.001 at OD 660 nm in turbidity of the cell suspension at said temperature per minute.

It should be appreciated that measurement of different lytic enzyme complexes against different test microorganisms can be expected to provide widely varying values for cell wall hydrolytic activity, and a high degree of variability has been found to exist. To avoid confusion the numerical values hereinafter provided for the cell wall hydrolytic activity will be those measured by the herein described test in tests against *Staphylococcus aureus*, (except of course when a different target microorganism is named). The inventors hereof recognize that the unit values they report are somewhat artificial and note that any lytic enzyme complex native to a strain of *Nocardiopsis dassonvillei* not exemplified herein should be tested against many target microorganisms to ascertain effectiveness against the mixed microflora present in (unwashed) laundry.

Cell count experiments have ascertained to the satisfaction of the inventors hereof that the turbidity decrease in cell suspension at 660 nm correlates well with the actual kill of the target organisms. The procedure is the same as described by K. Hayashi et. al., supra, except that all solutions excluding cell suspension are autoclaved and lytic enzyme solution is filter sterilized. At the end of incubation, reaction mixtures are serially diluted and plated on nutrient agar plates for survival bacterial counts.

Cell wall hydrolytic activity was also determined by the chemical, enzymatic assays.

(a). N-acetylmuramidase activity is measured by using cell wall of *Staphylococcus aureus* as the substrate and following the formation of N-acetylhexosamine (which is released from the cell wall). To 1 ml of *Staphylococcus aureus* cell wall suspension (which contains 1.6 mg cell wall made in 50 mM MES buffer, pH 6.0), 0.2 ml enzyme solution is added and the reaction mixture is incubated at 37° C. for 30 minutes with shaking. At the end of incubation time, the unused cell wall is removed by centrifugation and the supernatant is used to measure the concentration of released N-acetylhexosamine via p-dimethylaminobenzaldehyde (DMAB) method (J. L. Reissig et. al. Biol. Chem. 1955, 217:959–966). One unit is the amount of enzyme which releases 1 nmole N-acetylhexosamine from the cell wall at 37° C. per minute.

(b). Chitinase activity is measured by using chitin as the substrate and following the formation of N-acetylglucosamine in solution. 0.5 ml enzyme solution is mixed with a 0.5 ml chitin suspension which is composed of 4 mg chitin/ml in 0.1 M citric acid/0.2 M $Na_2HPO_4$ buffer, pH 6.5. The reaction mixture is then incubated at 37° C. for 90 minutes with vigorous shaking. At the end of incubation, the unused chitin is removed by centrifugation and the supernatant is then analyzed for N-acetylglucosamine concentration by DMAB method.

(c). Laminarinase activity is assayed by using laminarin as the substrate and following the increase of the reducing sugar concentration. Reaction mixtures are comprised of 0.1 ml laminarin (15 mg/ml in 0.1 M citric acid/0.2 M $Na_2HPO_4$ buffer, pH 6.0), 0.4 ml buffer and 0.2 ml enzyme solution. Mixtures are incubated for 10 minutes at 37° C. Then the reaction is terminated by addition of 0.3 ml cold $H_2O$ and cooled to room temperature in cold water. An aliquot (200 ul) of the solution is then used to measure the concentration of the reducing sugar via the micro Nelson method (R. G. Spiro. Method. Enzymology, 1966, Vol. 8:p.3).

As shown in the Table I, hereinafter provided the lytic enzyme complex from *Nocardiopsis dassonvillei* strain G102-3 (NRRL 18349) shows excellent activity towards the target organisms both in pH 7.0 buffer and in pH 9.5 buffer. Advantageously, the lytic enzyme complex from strain G102-3 performs better towards the target organisms at lower temperature of 15° C. vs. 40° C., which makes this lytic enzyme complex advantageous for low temperature laundering application, or room temperature rinse water application.

Table II shows that the lytic enzyme complex from strain G102-3 exhibits good lytic activity towards substrates in the presence of detergent components. Meanwhile, lytic enzyme from strain D38-3 shows excellent activity towards *Pseudomonas aeruginosa* in the presence of detergent components.

The data in Table I compared to the data in Table III and that in Table II with Table IV, demonstrates that the decrease in cell suspension turbidity correlates roughly with the true bacterial survival counts both in buffers and in detergent solutions.

The data presented in Table VI indicates that in the presence of detergent components Alcalase TM alone had some lytic effect, and the addition of the lytic enzyme complex of this invention increased the lysis to 75-93%.

Preparation of Lytic Enzyme Concentrate

*Nocardiopsis dassonvillei* strains G102-3 (NRRL 18349), G119-6 (NRRL 18350), and strain D38-3 (NRRL 18364) of the invention may be cultivated under aerobic conditions in a nutrient medium containing assimilable carbon and nitrogen together with other essential nutrients, the medium being composed in accordance with the principles of the known art, and per se forms no part of this invention.

Suitable carbon sources are carbohydrates, such as sucrose, glucose, and maltose, or carbohydrate containing materials such as cereal grains, malt, rice and sorghum. The carbohydrate concentration incorporated in the medium may vary widely, e.g., 1 to 15%, but usually 8-10% will be suitable, the percentage being calculated as equivalents of glucose.

The nitrogen source in the nutrient medium may be of an organic or inorganic nature. Among the organic nitrogen sources, quite a number are regularly used in fermentation processes involving the cultivation of actinomycetes. Illustrative examples are soybean meal, cotton seed meal, peanut meal, cornsteep liquor, and yeast extract. In addition, the nutrient medium should also contain the usual trace substances.

Since strains G119-6 and D38-3 of the invention are alkalophilic, their cultivation is conducted preferably at alkaline pH (8.5–9.0). The alkaline pH may be obtained by addition of suitable buffers, such as sodium carbonate or mixtures of sodium carbonate and sodium bicarbonate (after sterilization of the growth medium). For aerobic submerged cultivation of strains in tank fermentors, it is necessary to use artificial aeration. The rate of aeration may be that employed in conventional tank fermentation.

After fermentation, a liquid enzyme product may be produced from the fermentation broth by removal of coarse material from the broth and, if desired, through concentration of the broth by conventional method, e.g., evaporation at low temperature or by ultrafiltration. Finally, preservatives may be added to the concentrate.

As has been pointed out, the bacteriolytic enzyme complex of this invention can also be prepared by cultivation of a transformed microorganism cell which is made to contain a gene encoding for and expressing the lytic enzyme complex native to the *Nocardiopsis dassonvillei*, e.g., to one of the strains herein described, followed by recovery of the lytic enzyme from the culture broth. Thus, the microorganism to be cultivated is either a lytic enzyme complex producing strain of *Nocardiopsis dassonvillei* wherein the complex is a native enzyme (including mutants and variants of a wild strain productive of the lytic enzyme complex), or is a transformed host organism wherein the gene for the lytic enzyme complex has been inserted by recombinant DNA techniques. Such techniques are now well known in the art and generally comprise the following steps:

a) providing a suitable recombinant DNA cloning vector comprising DNA-sequences encoding functions facilitating gene expression and a DNA-sequence encoding the *Nocardiopsis dassonvillei* lytic enzyme complex;

b) transforming a suitable host organism with the cloning vector from step a); and c) culturing the transformed host in a suitable culture medium and recovering the lytic enzyme complex from the culture broth.

Preferred host organisms are strains of Nocardiopsis, Streptomyces, yeast, Aspergillus and Bacillus. It is especially preferred to use *A. oryzae* as the host according to the teachings in EP 238,023.

Enzyme Preparation

Solid enzyme preparations may be prepared from the purified and/or concentrated broth by precipitating with salts such as $Na_2SO_4$ or with water miscible solvents such as ethanol or acetone. Removal of water from the fermentation broth by suitable drying methods such as spray drying, evaporation under vacuum or even lyophilization may also be employed. The hydrolytic activity of lytic enzyme preparations obtained as of the date hereof has usually been in the range of about 1600 units/g of powder.

This crude product may be (partially) purified if enzyme concentrates of greater unit activity are desired in the market place. A suitable activity range for a detergent additive containing the lytic enzyme complex of this invention is 200 to 5,000 units per gm. of additive (solid form or liquid form).

Typical, known to the art detergent additive forms may be employed, particularly a non-dusting granulate, a stabilized liquid or a protected enzyme.

Non-dusting granulates may be produced, e.g., according to U.S. Pat. No. 4,106,991 or U.S. Pat. No. 4,661,452 and the granules may be coated according to principles known in the art.

Liquid form lytic enzyme complex preparations may be stabilized, e.g., by addition of propylene glycol, other polyols, sugars, sugar alcohols and boric acid or by other enzyme stabilizers known in the art.

Detergent Composition

The detergent compositions employed in practice the invention are comprised of known in the art surfactants which may be of the anionic, non-ionic, cationic or zwitterionic type, or a mixture of these. Typical examples of anionic surfactants are linear alkyl benzene sulfonate (LAS), alpha olefinsulfonate (AOS), alcohol ethoxy sulfate (AES) and natural soap of alkali metals.

Detergent compositions employed in practice of the invention, may contain other detergent ingredients known in the art, such as builders, bleaching agents, bleach activators, anti-corrosion agents, sequestering agents, anti-soil redeposition agents, perfumes, stabilizers for the enzymes and so on.

The detergent compositions may be formulated in any convenient form, such as powders, liquids, etc. The lytic enzyme may be stabilized in a liquid detergent by inclusion of enzyme stabilizers in the formulation, e.g., those mentioned above.

Most detergent compositions exhibit a pH in solution of 8–10.5. Due to their broad pH optimum, the lytic enzyme complexes of the invention are highly active in this range, as shown in FIGS. 1 and 2.

The detergent formulation employed in practice of this invention may include one or more other detergent enzymes in addition to lytic enzyme of the invention. Examples are protease, lipase, amylase and cellulase. Presence of protease is, of course, preferred.

The detergent composition formulations employed in practice of this invention can be expected to be known in the art. On the whole, the soapers have offered to the market place a great number of detergent formulations that have been optimized both as to cost and effectiveness. The details of any such detergent composition formulation form no part of this invention. Suffice it to say that the lytic enzyme complexes of this invention (and the alkaline Bacillus proteases as well) are compatible with commercially available detergent compositions formulations across the board, with the proviso that their employment in detergent formulations containing some bleaches and those which create a wash water pH exceeding pH 11 might not be practical. The usual pattern of the market place is for soaper companies to incorporate the enzyme(s) within their detergent formulation and in keeping with this pattern the enzyme manufacturers provide enzyme additives which comprise concentrated enzyme in non-dusting solid form or in stabilized liquid solution, the unit activity in the concentrate being adjusted so that the enzyme additive is from 0.5–5% by wt. of the detergent formulation (or by volume in liquid detergent formulations).

Thus, the detergent additive form of the lytic enzyme complexes of this invention fits into a well defined niche in the art, namely, as a concentrate of about 200 to 5000 units per gm. for incorporation into a (soaper's) detergent formulation as 0.5–5% by wt. or volume thereof so as to generate a lytic enzyme complex concentration of about 1000 to 20,000 unit preferably 2000 to 10,000 units per liter in the wash water. Comparably for direct addition into detergent containing wash water or into a rinse water free of detergent the additive may be supplied to consumers to generate the ultimate desired concentration, e.g., 2000 to 10,000 units per liter.

In a preferred mode of the invention an alkaline Bacillus protease in concentration of 0.5 to 3.0 Anson units per gram of additive, (or if more conveniently measured thereby an activity 0.5–3.0 KNPU/gm) may be included in the lytic enzyme mixture additive supplied to the soapers for inclusion in their detergent formulations, or alternatively to consumers for a separate addition to wash or rinse water. A protease containing additive may, of course, be added to the wash or rinse water separately from the lytic enzyme complex additive. In any event, concentrations of 2000–10,000 units per liter of lytic enzyme and of 0.01–0.15 Anson units per liter of protease in wash or rinse water are preferred. The enzyme mixture results in a combined or a synergistic improvement in the kill ratio of body odor generating microflora.

For further understanding of the invention the following specific examples are provided.

EXAMPLE I

*Nocardiopsis dassonvillei* strain G102-3 (NRRL 18349) was cultivated at 30° C. on a rotary shaking table (250 rpm) in 250 ml triple-baffled Erlenmeyer flasks containing 50 ml of medium of the following composition:

Composition of the medium in grams per liter:

| | |
|---|---|
| Maltodextrin M-100 | 20 |
| Soy bean meal | 20 |
| Yeast extract | 5 |
| NaCl | 2 |

Before sterilization, the pH of the medium was adjusted to 7.0 by the addition of a few drops of 0.1 M NaOH. After 2 to 4 days of incubation, the lytic enzyme activity of the broth was determined by using the turbidity reduction method described above. The lytic activity of the G102-3 broth was 16.2 unit/ml with *Staphylococcus aureus* as the substrate after 72 hours incubation. *Nocardiopsis dassonvillei* strain G119-6 (NRRL 18350) and strain D38-3 (NRRL 18364) were also cultivated at 30° C. as described, except for the following differences:

Composition of the medium in grams per liter:

| | |
|---|---|
| Maltodextrin M-100 | 20 |
| Soy bean flour | 20 |
| Yeast extract | 2 |
| $K_2HPO_4$ | 1 |

-continued

| | |
|---|---|
| MgSO$_4$—7H$_2$O | 1 |

After sterilization, the pH of the medium was adjusted to 8.5–9.0 by the addition of 5 ml of 1 M solution of sodium carbonate/sodium bicarbonate buffer, pH 9.2. After 114 hours of incubation, the broth of strain G119-6 had a lytic activity of 17.8 unit/ml with the viable *Staphylococcus aureus* as the substrate. After 142 hours of incubation, the broth of strain D38-3 had a lytic activity of 47.5 unit/ml with the viable *Pseudomonas aeruginosa* as the substrate.

EXAMPLE II

The lytic activity of strain G-102-3 lytic enzyme from Example I is depicted in Table 1 when different microorganisms were used as the substrates. The target organisms, *Micrococcus kristinae, Micrococcus sedentarius, Pseudomonas aeruginosa* and *Staphylococcus aureus* were suspended in 62.5 mM phosphate buffer, pH 7.0 and 50 mM borate buffer, pH 9.5 to give an initial OD at 660 nm of 0.8. Lytic reactions were carried out with 3 units per ml of the reaction mixture at 15° C. and 40° C. with 10 minutes incubation. At the end of incubation, the reduction of turbidity of the cell suspensions was measured at 660 nm by use of a spectrophotometer.

TABLE I

| | | Δ OD 660 nm | |
|---|---|---|---|
| Substrate organism | | at 15° C. | at 40° C. |
| *M. kristinae* | in pH 7 buffer | 0.181 | 0.174 |
| | in pH 9.5 buffer | 0.154 | 0.155 |
| *M. sedentarius* | in pH 7 buffer | 0.237 | 0.148 |
| | in pH 9.5 buffer | 0.235 | 0.123 |
| *Pseud. aeruginosa* | in pH 7 buffer | 0.264 | 0.160 |
| | in pH 9.5 buffer | 0.224 | 0.161 |
| *Staph. aureus* | in pH 7 buffer | 0.289 | 0.169 |
| | in pH 9.5 buffer | 0.272 | 0.147 |

EXAMPLE III.

The lytic activity of strain G102-3 lytic enzyme and D38-3 lytic enzyme (from Example I) in the presence of detergent is depicted in Table II when different microorganisms were used as the substrates. The target organisms, *Micrococcus kristinae, Micrococcus sedentarius, Pseudomonas aeruginosa,* and *Staphylococcus aureus* were suspended in detergent solution which was made by addition of 1.5 g detergent powder into 1 l of deionized H$_2$O and then adjusted to 9° dH German hardness by addition of CaCl$_2$ and MgCl$_2$. The detergent formulation used in the tests was Tide ™ with no phosphate.

Lytic reactions were carried out at 15° C. and 40° C. with 10 minutes incubation at 3 units per ml of the lytic enzyme complex. At the end of incubation, the reduction of turbidity of the cell suspensions was measured at 660 nm by use of a spectrophotomer.

TABLE II

| | Δ OD 660 nm | | | |
|---|---|---|---|---|
| | G102-3 enzyme | | D38-3 enzyme | |
| Substrate organism | at 15° C. | at 40° C. | at 15° C. | at 40° C. |
| *M. kristinae* | 0.218 | 0.188 | 0 | 0 |
| *M. sedentarius* | 0.242 | 0.159 | 0.031 | 0.087 |
| *Pseud. aeruginosa* | 0.233 | 0.166 | 0.324 | 0.495 |
| *Stah. aureus* | 0.372 | 0.252 | 0.069 | 0.231 |

EXAMPLE IV

To assess the actual number of microorganisms which were lysed by lytic enzyme produced from strain G102-3, the following viable cell count experiments were carried out and the results are shown in Table III. Overnight-grown substrate organisms, *Micrococcus kristinae* and *Staphylococcus aureus,* were suspended in 50 mM borate buffer, pH 9.5 to ~10$^4$ CFU/ml. To 2 ml of cell suspension, 0.5 ml of appropriately diluted enzyme solution (to 3 units/ml of reaction mixture) was added and incubated at 15° C. or 40° C. for 10 minutes with periodic mixing. All the solutions including enzyme were sterile. At the end of incubation, the reaction mixtures were serially diluted and plated on nutrient agar plates for survival bacterial counts.

TABLE III

| | % Kill | |
|---|---|---|
| Substrate organism | at 15° C. | at 40° C. |
| *M. kristinae* | 35 | 44 |
| *Stah. aureus* | 47 | 53 |

EXAMPLE V

The actual number of microorganisms which were lysed by lytic enzyme from strain G102-3 at 3 units/ml of reaction mixture in the presence of detergent components (1.5 g/l) was determined by an experiment similar to that in Example IV except that *Micrococcus kristinae* and *Staphylococcus aureus* were suspended in the detergent solution to approximately 10$^4$ CFU/ml which was described in Example III. The results are shown in Table IV.

TABLE IV

| | % Kill | |
|---|---|---|
| Substrate organism | at 15° C. | at 40° C. |
| *M. kristinae* | 64 | 58 |
| *Staph. aureus* | 60 | 52 |

It is evident that in buffer or in detergent solution lytic enzyme from strain G102-3 consistently lyses 35–64% of viable microorganisms. The lytic enzyme is most effective in detergent solution.

EXAMPLE VI

A comparative lytic activity of lytic enzymes from strain G102-3, Mutanolysin and N-acetylmuramidase from *Streptomyces rutgersensis* (ATCC 3350) towards target microorganisms in the presence of detergent components is depicted in Table V. *Lactobacillus plantarum* (ATCC 8014) was the substrate organism for strain G102-3 lytic enzyme and Mutanolysin whereas *Streptococcus faecium* (ATCC 8043) was the substrate for G102-3 lytic enzyme and *Streptomyces rutgersensis* (ATCC 3350) enzyme. It is known that *Lactobacillus plantarum* and *Streptococcus faecium* are the best target organism for Mutanolysin and N-acetylmuramidase from *Streptomyces rutgersensis*, respectively. The detergent solution was as described in Example III, and the same 3 units/ml of enzyme activity level was used throughout the experiment while reactions were carried at 15° C.

TABLE V

| Enzyme | Δ OD 660 nm | |
|---|---|---|
| | Lactobacillus plantarum | Streptococcus faecium |
| From strain G102-3 | 0.219 | 0.121 |
| Mutanolysin from *S. globisporus* | 0.083 | N.D. |
| From *S. rutgersensis* | N.D. | 0.0 |

EXAMPLE VII

The combination effect of Alcalase TM and lytic enzyme from strain G102-3 on viable microorganisms was demonstrated in the following experiments.

When *Micrococcus kristinae* and *Staphylococcus aureus* were suspended in detergent solution as described in Example V, 0.05 AU/l of Alcalase TM was dosed in to examine any additional lytic effect of Alcalase TM in detergent solution. As shown in Table VI, Alcalase TM alone in detergent does have some lytic effect. However, when lytic enzyme produced by G102-3 was added at 3 units/ml (3000 units/l) in combination with 0.05 AU/l of Alcalase TM, an average of 75–93% lysis was achieved.

TABLE VI

| | M. kristinae | Staph. aureus |
|---|---|---|
| Detergent alone | 0% Kill | 0% Kill |
| Alcalase TM + Detergent | 46–51 | 36–65 |
| Lytic enzyme + Alcalase TM + Detergent | 75–93 | 85–89 |

An increased dose of Alcalase TM (up to 0.2 AU/l) in detergent did not result in a significant increase in lysis of *M. Kristinae* or *S. aureus*.

EXAMPLE VIII

The synergistic effect of Savinase TM or Esperase TM with lytic enzyme from strain G102-3 on lysis of *Staphylococcus aureus* in liquid detergent was demonstrated in the following experiments.

Liquid detergent, Wisk TM (alkaline pH solution), was made to the commercial level. The target organism *Staphylococcus aureus* was suspended directly in the detergent solution to an initial $OD_{660} \sim 0.8$. Savinase TM or Esperase TM was dosed in at the commercial level (0.06 KNPU/l) as described in Example VII. The lytic reaction with 3 units/ml was monitored by the decrease in turbidity at 660 nm. As shown in Table VII, Savinase TM or Esperase TM alone in liquid detergent has no lytic effect on the organism. It is also evident that G102-3 lytic enzyme expresses good lytic activity in both powder detergent (Example VII) and liquid detergent. A synergistic effect of lytic enzyme from G102-3 with Savinase TM or Esperase TM on lysis of *Staphylococcus aureus* seems to have been obtained in the Wisk TM.

TABLE VII

| Conditions | % Lysis | |
|---|---|---|
| | 15° C. | 40° C. |
| Detergent alone | 0 | 0 |
| Savinase TM + Detergent | 0 | 0 |
| Esperase TM + Detergent | 0 | 0 |
| Lytic enzyme + Detergent | 0 | 36 |
| Lytic enzyme + Savinase TM + Detergent | 7 | 90 |
| Lytic enzyme + Esperase TM + Detergent | 3 | 91 |

EXAMPLE IX

Microorganisms which are known to be pathogens, opportunists, common skin and/or clothing contaminants and/or difficult to be lysed by egg-white lysozyme were tested as the substrate organisms for strain G102-3 lytic enzyme and strain D38-3 lytic enzyme. Common skin and/or clothing contaminants were isolated in our laboratory and designated as NOVO 1, 8, 12, 13. A comparison was made between the effect of 1 mg/ml of egg-white lysozyme (from Sigma) and that of 1 mg lyophil from crude fermentation broth/ml of reaction mixture. As shown in Table VIII, in most cases lytic enzyme produced by strain G102-3 is definitely much more effective than the egg-white lysozyme, whereas D38-3 lytic enzyme is demonstrated to be extremely potent to *Pseudomonas aeruginosa* cells.

TABLE VIII

| Substrate organism | G102-3 lytic enzyme (% lysis) | D38-3 lytic Enzyme (% lysis) | egg-white lysozyme (% lysis) |
|---|---|---|---|
| *Lactobacillus plantarum* (ATCC 8014) | 50 | 8 | 0 |
| *Micrococcus kristinae* (ATCC 27570) | 20 | 0 | 2 |
| *Micrococcus sedentarius* (ATCC 14392) | 30 | 11 | 0 |
| *Pseudomonas aeruginosa* (ATCC 9027) | 98 | 99 | 0 |
| *Streptococcus faecium* (ATCC 8043) | 29 | 0 | 2 |
| *Streptococcus mutans* (ATCC 25175) | 0 | 0 | 17 |
| *Staphylococcus aureus* (ATCC 6538) | 35 | 19 | 0 |
| *Saccharomyces cerevisiae* (Anheuser Busch brewer's yeast) | 5 | 3 | 9 |
| *Staphylococcus aureus* (NOVO-1) | 47 | 2 | 7 |
| *Micrococcus epidermidis* (NOVO-8) | 4 | 7 | 0 |
| *Micrococcus sp.* (NOVO-12) | 4 | 12 | 0 |
| *Micrococcus sp.* (NOVO-13) | 13 | 0 | 0 |

EXAMPLE X

The lytic enzyme produced by strain G102-3 was identified as a mixture of enzymes, namely N-acetylmuramidase, chitinase and laminarinase, whereas the lytic enzyme produced by strain D38-3 contained chitinase and laminarinase.

Their individual enzyme activity from fermentation broth of Example I are tabulated in Table IX.

TABLE IX

| | G102-3 enzyme (mu/ml) | D38-3 enzyme (mu/ml) |
|---|---|---|
| N-acetylmuramidase | 12 | 0 |

TABLE IX-continued

| | G102-3 enzyme (mu/ml) | D38-3 enzyme (mu/ml) |
|---|---|---|
| Chitinase | 5.0 | 0.33 |
| Laminarinase | 80 | 70 |

We claim:

1. A purified bacteriolytic enzyme preparation derived from a strain of *Nocardiopsis dassonvillei* which
   a) has the ability to hydrolyze bacterial cell walls of *Micrococcus sedentarius, Pseudomonas aeruginosa* and *Staphylococcus aureus*; and
   b) retains at least 70% of its maximum lytic activity in the pH range of 8-10, as measured towards the substrate organisms *Pseudomonas aeruginosa* and *Staphylococcus aureus*.

2. The bacteriolytic enzyme preparation according to claim 1, wherein the *Nocardiopsis dassonvillei* strain is selected from the group consisting of those having deposit numbers NRRL 18350, NRRL 18364 and mutants thereof which retain the ability to produce the enzyme preparation.

3. The bacteriolytic enzyme preparation according to claim 1 which also has the ability to hydrolyze bacterial cell walls of *Micrococcus kristinae*.

4. The bacteriolytic enzyme preparation according to claim 3, wherein the *Nocardiopsis dassonvillei* strain is NRRI 18349 or a mutant thereof which retain the ability to produce the enzyme preparation.

5. The bacteriolytic enzyme preparation according to claim 1, further comprising an alkaline Bacillus protease.

6. The bacteriolytic enzyme preparation according to claim 5, which contains at least 200 units of bacteriolytic activity per gram of the preparation and from 0.5 to about 3.0 Anson units of the Bacillus protease per gram of the preparation.

7. A detergent composition which comprises the bacteriolytic enzyme preparation according to claim 1 and a surfactant.

8. The detergent composition according to claim 7, further comprising an alkaline Bacillus protease.

9. A process for preparing a bacteriolytic enzyme preparation, comprising
   (a) cultivating a bacteriolytic enzyme preparation producing strain of *Nocardiopsis dassonvillei* selected from the group consisting of those strains of *Nocardiopsis dassonvillei* having deposit numbers NRRL 18349, NRRL 18350, NRRL 18364 and bacteriolytic enzyme preparation producing mutants thereof aerobically under submerged conditions in the presence of carbon and nitrogen sources, and
   (b) recovering the bacteriolytic enzyme preparation from the culture broth.

10. A biologically pure culture of a strain of *Nocardiopsis dassonvillei* having deposit numbers NRRL 18349, NRRL 18350, NRRL 18364 and bacteriolytic enzyme preparation producing mutants thereof; and 11. A method for reducing body odor of clothes, comprising washing or rinsing clothes in wash water or rinse water comprising at least 1,000 units of the bacteriolytic enzyme preparation according to claim 1.

* * * * *